(12) United States Patent
Lee et al.

(10) Patent No.: US 6,397,107 B1
(45) Date of Patent: May 28, 2002

(54) APPARATUS FOR EMBOLIC TREATMENT USING HIGH FREQUENCY INDUCTION HEATING

(75) Inventors: Kyu Ho Lee, Seoul; Jae Kun Lee, Gumi, both of (KR)

(73) Assignee: Bokwang Co., Ltd. (KR)

( * ) Notice: Subject to any disclaimer, the term of this patent is extended or adjusted under 35 U.S.C. 154(b) by 0 days.

(21) Appl. No.: 09/446,779

(22) PCT Filed: Apr. 27, 1999

(86) PCT No.: PCT/KR99/00199

§ 371 (c)(1),
(2), (4) Date: Apr. 12, 2000

(87) PCT Pub. No.: WO99/55398

PCT Pub. Date: Nov. 4, 1999

(30) Foreign Application Priority Data

Apr. 27, 1998 (KR) ............................................. 98-14935

(51) Int. Cl.[7] .................................................. A61F 2/00
(52) U.S. Cl. ......................................... 607/103; 606/65
(58) Field of Search ................... 607/96, 98, 101–103, 607/113, 61, 65; 219/211, 529

(56) References Cited

U.S. PATENT DOCUMENTS

| | | | | |
|---|---|---|---|---|
| 4,066,065 A | * | 1/1978 | Kraus | |
| 4,454,883 A | * | 6/1984 | Fellus | |
| 4,527,550 A | * | 7/1985 | Ruggera et al. | |
| 5,019,076 A | * | 5/1991 | Yamanashi et al. | 606/45 |
| 5,109,843 A | * | 5/1992 | Melvin et al. | 607/2 |
| 5,160,828 A | * | 11/1992 | Olsen | 219/211 |
| 5,741,316 A | * | 4/1998 | Chen et al. | 607/61 |
| 6,238,421 B1 | * | 5/2001 | Gunther et al. | 607/13 |

* cited by examiner

Primary Examiner—Roy D. Gibson
(74) Attorney, Agent, or Firm—Baker Botts LLP

(57) ABSTRACT

An apparatus for embolic treatment including a high frequency power source and at least one induction coil connected to the high frequency power source which is positioned around the vicinity of diseased vasculature of the body of a patient for generating an eddy current in the metallic coil inserted into the vascular malformation of the diseased vasculature. The eddy current in the metallic coil generates heat which coagulates and contracts the vascular malformation.

8 Claims, 5 Drawing Sheets

APPARATUS FOR EMBOLIC TREATMENT USING HIGH FREQUENCY INDUCTION HEATING

BACKGROUND OF THE INVENTION

1. Field of the Invention

The invention relates to an apparatus for embolic treatment, and more particularly to an apparatus for embolic treatment using high frequency induction heating to embolize cerebral aneurysms by filling and fixing a metallic coil in cerebral vascular malformations.

2. Description of the Related Art

Vascular malformations include aneurysms and arterio-venous malformations which may develop in any part of a body. Since aneurysms which develop in the aorta, and the vasculature of the abdominal and cerebral regions can be fatal, they must be operated on.

One conventional treatment for cerebral aneurysms includes searching for the problematic area in the cerebral arteries by photographing the cerebral vasculature of the patient, making an incision in the skull following total body anesthetizes, exposing the cerebral aneurysm, and then banding the neck of the aneurysm with a specialized clip. The surgical procedure for the cerebral incision and the banding of the neck of the aneurysm, has high risk and the procedure takes an unduly long time. Further, post-op recovery is lengthy and requires intensive follow-up medical care, and the patient may be subject to attacks of cerebral pain as an aftereffect.

In order to resolve the above-noted problems, non-invasive treatments have been proposed to replace such risky operations. FIG. 1. is a schematic illustration showing an operation method for embolizing a vascular malformation using a conventional apparatus for the embolic treatment. Referring to FIG. 1, a conventional method for embolizing a cerebral aneurysm or vascular malformation (6) includes filling and fixing a metallic coil (3) into the malformation (6) using a fine catheter (1) while photographing the cerebral blood vessel in question without a head incision. Such non-invasive vascular operations have been applied not only to treatment of cerebral aneurysm and arterio-venous malformations, but also to treatment of vascular disease in other parts of the body.

However, follow-up inspection by photography of the vascular malformation treated with known conventional methods as described above, after a predetermined period such as 6 months, often reveals unstable embolic states in which blood flowing along the vessel is recirculated in the malformation embolized in its early stage. Consequently, coils are sometimes inserted into vascular malformations excessively in the initial operation to ensure long time maintenance of the complete embolic state, which may be fatal as the target malformation such as an aneurysm can rupture due to such excessive insertion of the coil.

Additionally, if the neck of an aneurysm is enlarged to a high degree, conventional embolic treatment may not work as coil-insertion cannot be adequately applied to the malformation. Further problems associated with conventional embolic treatment include the undesired migration of the coil from the inserted malformation to other parts of the cerebral vasculature.

SUMMARY OF THE INVENTION

Accordingly, the object of the present invention is to provide a novel apparatus for embolic treatment using high frequency induction heating in order to completely embolize a vascular malformation.

To accomplish the above object, the present invention provides an apparatus for use in an operating method for embolizing an aneurysm by filling the vascular malformation with a metallic coil, comprising, a high frequency power source, and at least one induction coil connected to a high frequency power source and positioned on the body of a patient in the vicinity of the diseased vasculature to generate an eddy current in a metallic coil inserted into the vascular malformation.

BRIEF DESCRIPTION OF THE DRAWINGS

Reference is made to the drawings for purposes of illustration only and not by way of limitation, and they illustrate the following.

DETAILED DESCRIPTION OF PREFERRED EMBODIMENTS

The present invention will now be described in further detail by way of example with reference to the accompanying drawings.

Figure 2:
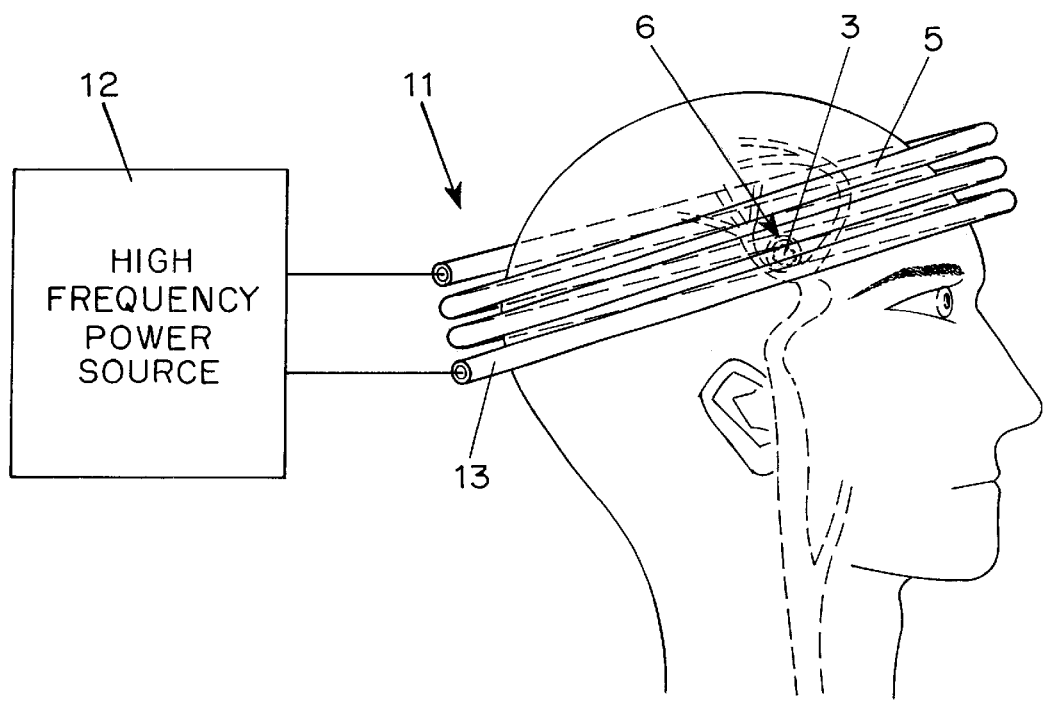
FIG. 2 is a schematic illustration depicting a method for treating a vascular malformation using the embolic apparatus according to the present invention.

FIG. 2. shows the embolic apparatus (11) according to the present invention. Apparatus (11) comprises a high frequency power source (12), and an induction coil (13) connected to the high frequency power source (12) and positioned around the head of a patient.

High frequency power source (12) supplies high frequency varied from 400 KHz to 40 MHz, voltage varied from 1 KV to 10 KV, and current varied from 10 A to 60 A. In the illustrated embodiment, induction coil (13) is typically made from copper pipe and coiled around the diseased parts of the head of a patient. One skilled in the art will appreciate that the induction coil of this embodiment may be suitably adapted to conform to other diseased parts of the body of a patient.

The method for using the embolic apparatus of the present invention in embolic treatment will be described with particular reference to FIGS. 1 and 2.

Initially, the head of a patient is fixed after the patient is anesthetized. Fine catheter (1) is inserted into the vascular malformation (6) of the head by use of angiography. Metallic coil (3) is then placed in vascular malformation (6) through fine catheter (1). As shown in FIG. 2, after the placement of coil (3) in malformation (6) is complete, induction coil (13) is positioned to surround the head. As power source (12) is turned on, high frequency current flows along induction coil (13) and a high frequency induction magnetic field is formed around the induction coil thereby forming an eddy current in metallic coil (3) which heats the metallic coil through eddy current loss. As a result, the heat produced in metallic coil (3) is transferred to the walls of vascular malformation (6) and the tissue of the malformation coagulates and contracts around coil (3). In this manner, the vascular malformation (6) is suitably embolized.

According to the foregoing description, high frequency induction heating (100 C) at a metallic coil was performed under conditions of 13.56 MHz/1.0 KW/2 min or 3.39 MHz/3.0 KW/5 min using an induction coil made from copper tubing and in the form of a Helmholtz coil having a diameter of 27 cm. The results in tissue coagulation around the metallic coil in the malformation was satisfactory.

FIGS. 3A to 3G show the preferred embodiments of the induction coils for use in the embolic apparatus of the present invention.

Figure 3A:
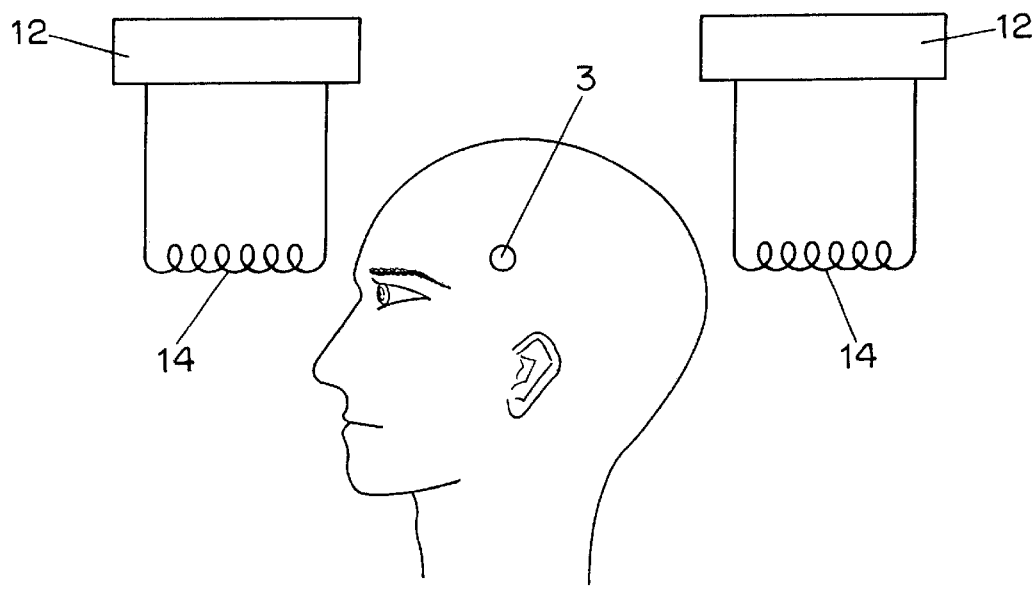
FIGS. 3A to 3G are schematic illustrations depicting various embodiments of high frequency coils used for the embolic apparatus according to the present invention.

FIG. 3A illustrates an embodiment which heats metallic coil (3) with a high frequency magnetic field generated from a pair of induction coils (14) connected to two high frequency power sources (12), respectively. As shown in FIG. 3A, the pair of induction coils (14) are positioned symmetrically and centered around metallic coil (3).

Figure 3B:
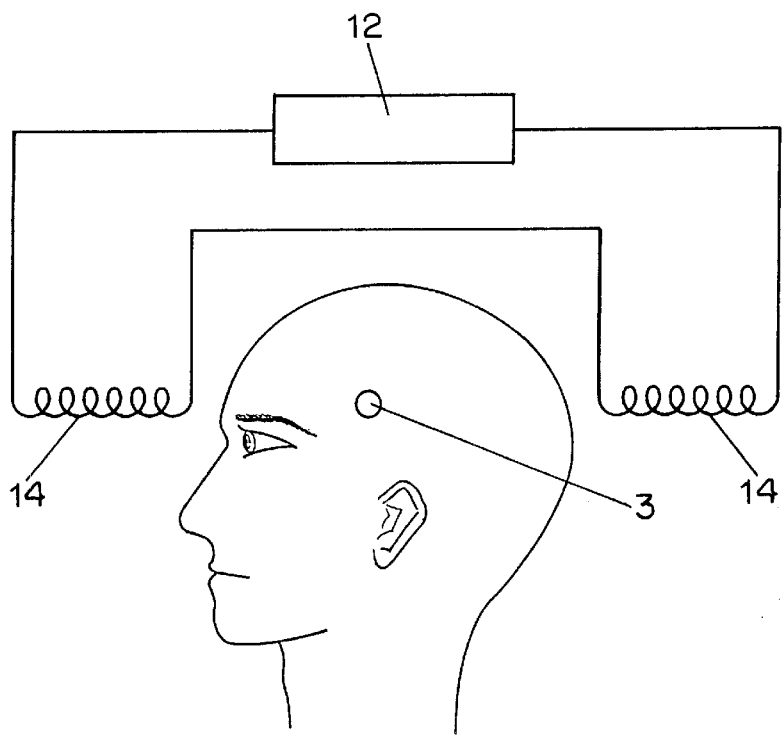

FIG. 3B illustrates a variation to the embodiment shown in FIG. 3A in which coil (3) is heated by a high frequency magnetic field generated from a pair of induction coils (14) which are connected in series to each other using one high frequency power source (12).

Figure 3C:
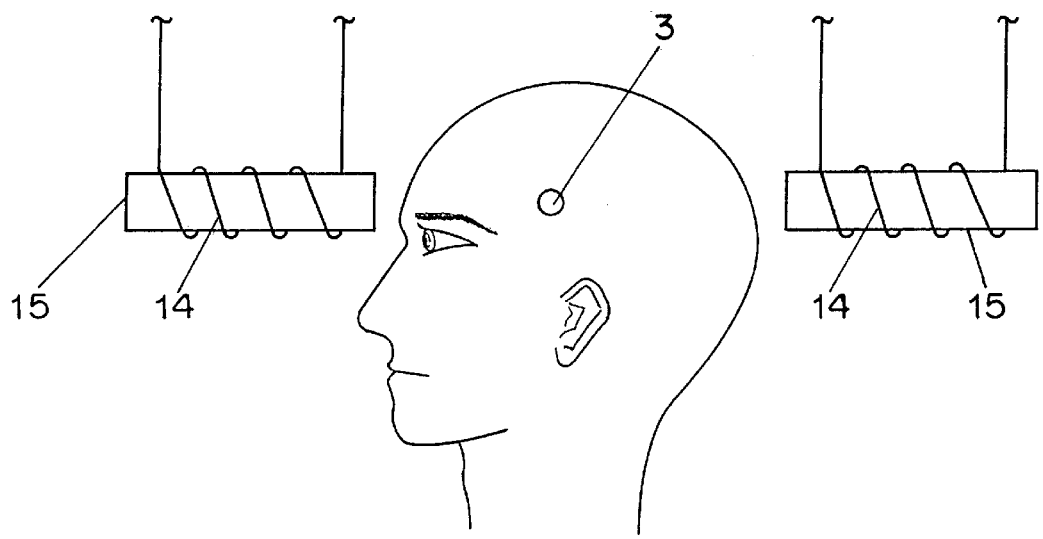
Figure 3D:
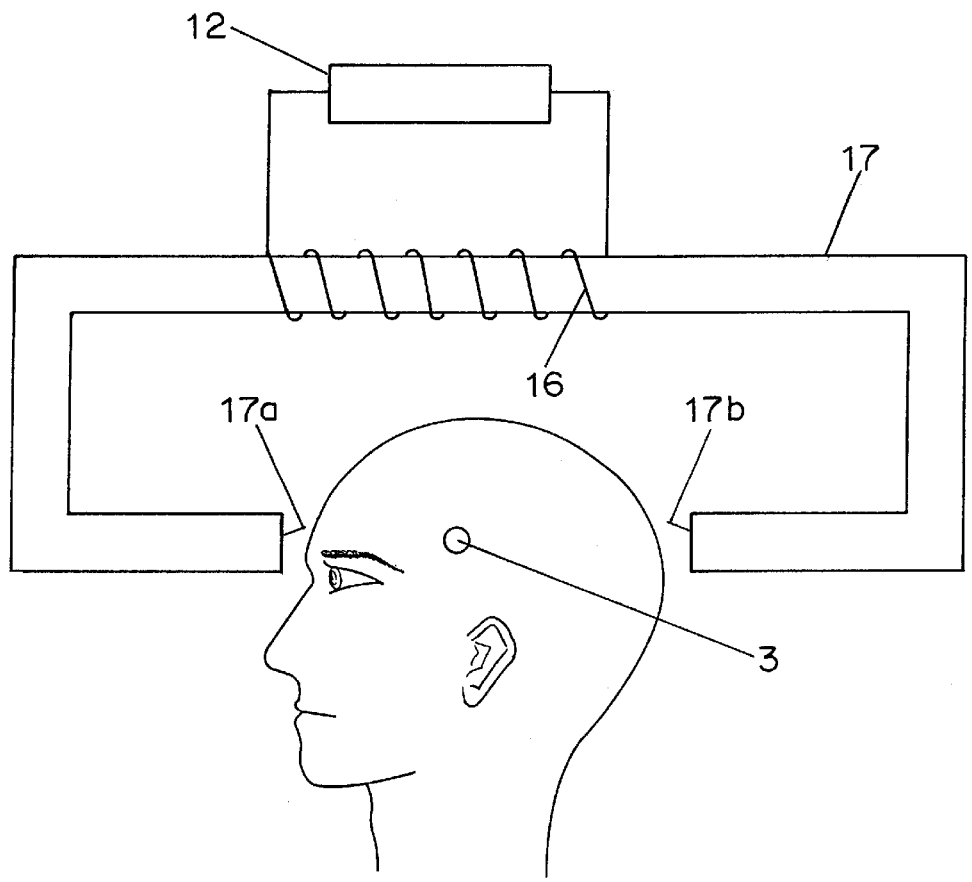

FIGS. 3C and 3D depict embodiments which generate more stronger magnetic fields than the forgoing embodiments using magnetic cores (15 or 17). The magnetic core is preferably made of a ferromagnetic material or a soft magnetic material. FIG. 3C shows induction coils (14) adapted around magnetic cores (15). FIG. 3D illustrates induction coil (16) adapted around magnetic core (17) such that both free ends (17a, 17b) of magnetic core (17) are positioned symmetrically and centered around metallic coil (3).

Figure 3E:
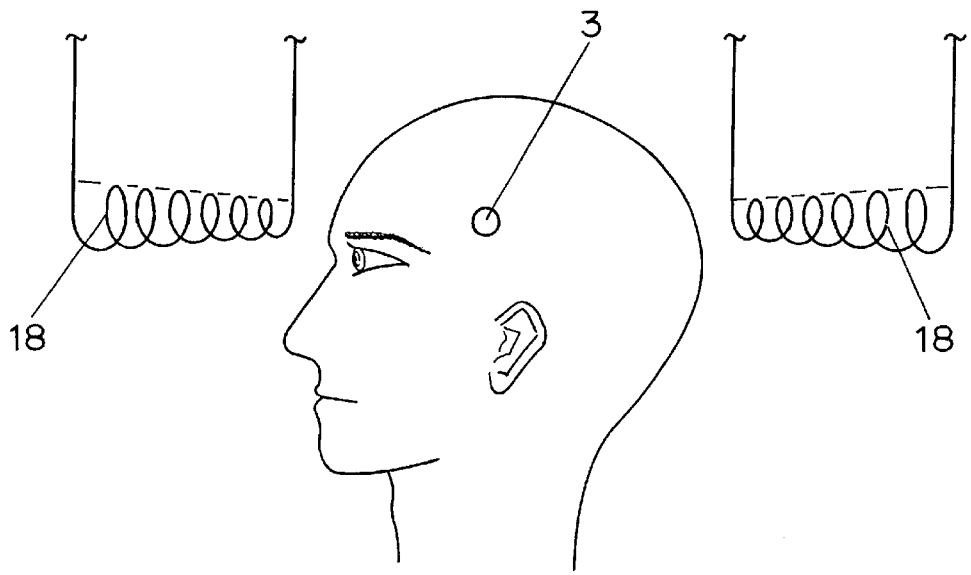
Figure 3F:
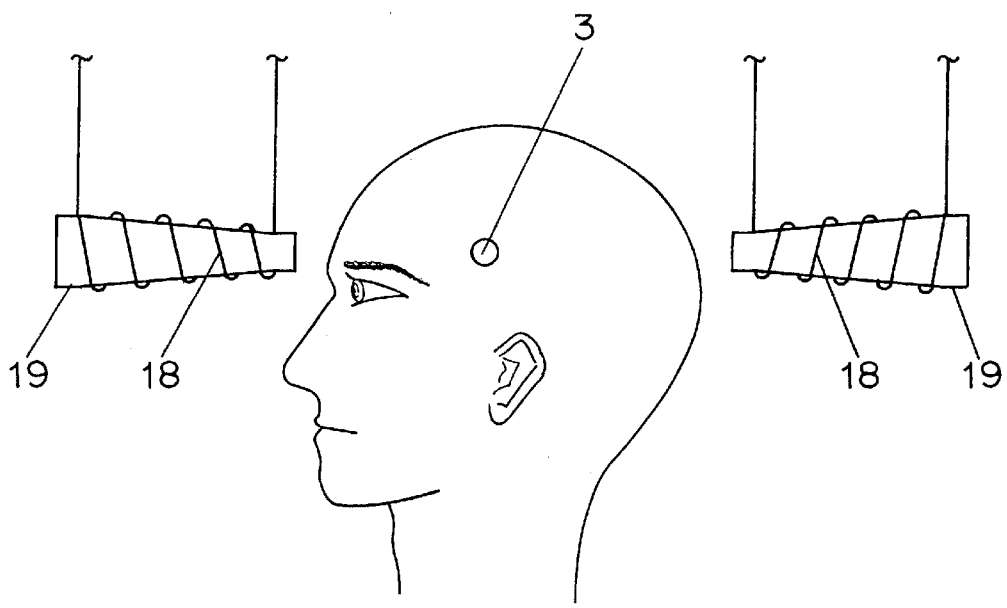

FIG. 3E illustrates an embodiment in which induction coil (18) is in the form of a cone and not cylindrical; and FIG. 3F illustrates another embodiment having induction coil (18) adapted around a magnetic core (19) which has a similar conical form. FIG. 3E shows a pair of induction coils (18) in the form of a cones converging toward, positioned symmetrically and centered around metallic coil (3). FIG. 3F depicts induction coils (18) wrapped around magnetic cores (19) in the shape of cones. Induction coils (18) allow more focus on metallic coil (3) by presenting a relatively stronger magnetic field.

Figure 3G:
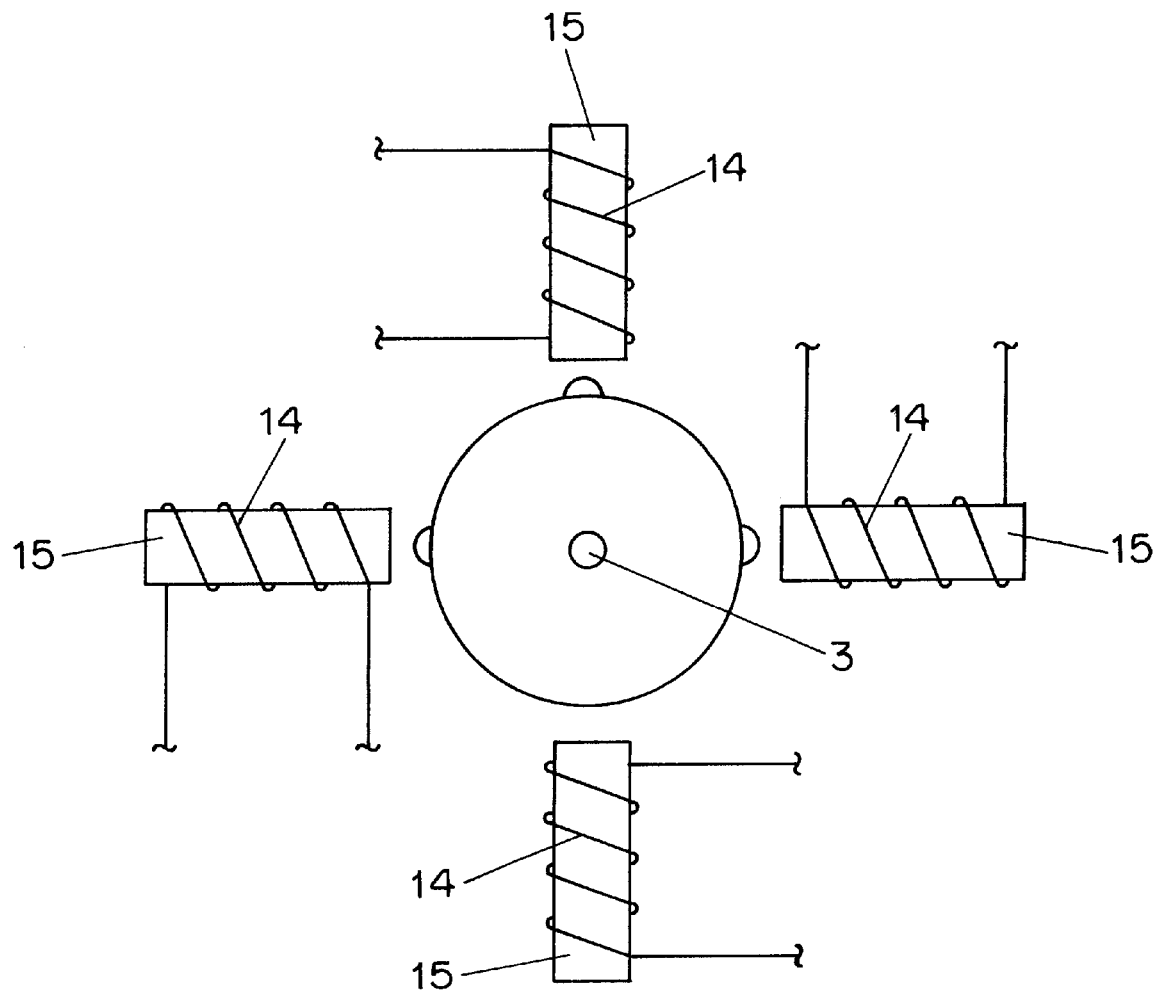

FIG. 3G illustrates an embodiment having four induction coils (14) each wrapped around respective magnetic cores (15). This arrangement generate an even more stronger eddy current in metallic coil (3).

According to the embolic apparatus of the present invention, eddy current generated in the metallic coil produces heat which results in coagulation and contraction of a vascular malformation around the coil by induction heating. The present apparatus is able to sufficiently embolize vascular malformations, and provides a solution to various problems associated with excessive insertion of metallic coils into malformation to prevent an incomplete embolic state, the migration of the metallic coil, and restrictions on using a metallic coil due to large neck vascular malformations.

The foregoing invention has been described in terms of preferred embodiments. However, those skilled, in the art will recognize that many variations to such embodiments are possible. Such variations are intended to be within the scope of the present invention and the appended claims.

What is claimed is:

1. An apparatus for embolizing an aneurysm, comprising:
   a metallic coil adapted for insertion into a vascular malformation for embolizing the vascular malformation;
   a high frequency power source; and
   at least one induction coil connected to said high frequency power source and positioned on the body of a patient in the vicinity of diseased vasculature to generate an eddy current in said metallic coil upon insertion of said metallic coil into said vascular malformation.

2. The apparatus of claim 1, wherein said high frequency power source supplies high frequency varied from 400 KHz to 40 MHz, voltage varied from 1 KV to 15 KV. and current varied from 10 A to 60 A.

3. The apparatus of claim 1 or 2, wherein said induction coil is adapted to be positioned to surround said vicinity of said diseased vasculature of said body of said patient.

4. The apparatus of claim 1 or 2, wherein at least a pair of induction coils are positioned symmetrically and centered around said metallic coil inserted in said vascular malformation.

5. The apparatus of claim 4, wherein each of said induction coils are wrapped around a magnetic core.

6. The apparatus of claim 1 or 2, wherein said induction coil is wrapped around a magnetic core such that both free ends of said magnetic core are positioned symmetrically and centered around said metallic coil inserted in said vascular malformation.

7. The apparat of claim 1 or 2, wherein at least a pair of induction coils are each in the shaped of a cone, which converge toward said metallic coil and are positioned symmetrically and centered around said metallic coil inserted in said vascular malformation.

8. The apparatus of claim 7, wherein each of said induction coils are wrapped around a magnetic core in the shape of a cone.

\* \* \* \* \*

UNITED STATES PATENT AND TRADEMARK OFFICE
CERTIFICATE OF CORRECTION

PATENT NO. : 6,397,107 B1
DATED : May 28, 2002
INVENTOR(S) : Lee et al.

It is certified that error appears in the above-identified patent and that said Letters Patent is hereby corrected as shown below:

Title page,
Item [56], References Cited,
U.S. PATENT DOCUMENTS, insert
-- 4121592    Oct. 1978    Whalley
4323056    Apr. 1982    Borrelli et al.
4662359    May 1987    Gordon
4674481    Jun. 1987    Boddie, Jr. et al.
4679561    Jul. 1987    Doss
4920978    May 1990    Colvin
4945912    Aug. 1990    Langberg
5401941    Mar. 1995    Mauve et al.
5441746    Aug. 1995    Chagnon
5492122    Feb. 1996    Button et al.
5507743    Apr. 1996    Edwards et al.
5807395    Sep. 1998    Mulier et al. --

FOREIGN PATENT DOCUMENTS, insert
-- 7900836    Oct. 1979    PCT
0040512    Nov. 1981    EPO
2-92371    Apr. 1990    Japan Abstr.
279820    June 1990    Germany
9007322    July 1990    PCT
07123715    May 1996    EPO
9707736    Mar. 1997    PCT
9722290    June 1997    PCT Abstr. --

Item [73], Assignee, "Bokwang Co., Ltd" should read
-- Phoenix Display Electronics Co., Ltd. --

Figure 1:
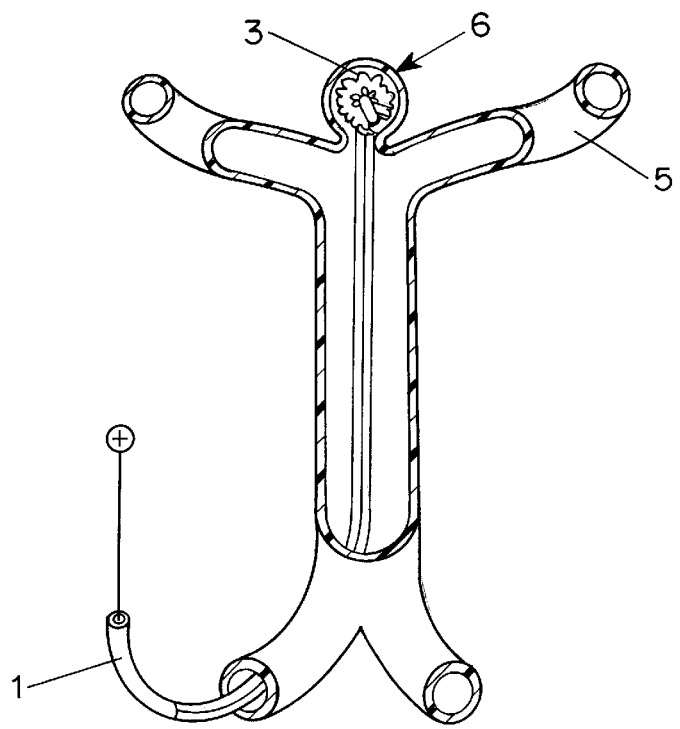
FIG. 1 is a schematic illustration depicting a method for treating a vascular malformation using a conventional embolic apparatus.

Column 1,
Line 17, "regions" should read -- regions, --
Line 24, "anesthetizes," should read -- anesthesia, --
Line 25, "aneurysm," should read -- aneurysm --
Line 33, "FIG. 1." should read -- FIG. 1 --

Column 2,
Line 6, "coil, comprising," should read -- coil comprising --
Line 38, "KHz" should read -- kHz --
Line 39, "KV" (both occurrences) should read -- kV --
Line 39, "10" should read -- 10 -- (no bold)
Line 67, "(100 C)" should read -- (100º C) --

UNITED STATES PATENT AND TRADEMARK OFFICE
CERTIFICATE OF CORRECTION

PATENT NO. : 6,397,107 B1
DATED : May 28, 2002
INVENTOR(S) : Lee et al.

It is certified that error appears in the above-identified patent and that said Letters Patent is hereby corrected as shown below:

Column 3,
Lines 1 and 2, "KW" should read -- kW --
Line 5, "was" should read -- were --
Line 22, "more" should be deleted
Line 43, "generate" should read -- generates --; and "more" should be deleted Column 4,
Line 7, "skilled," should read -- skilled --
Line 41, "apparat" should read -- apparatus --
Line 42, "shaped" should read -- shape --

Signed and Sealed this

Twenty-ninth Day of October, 2002

*Attest:*

*Attesting Officer*

JAMES E. ROGAN
*Director of the United States Patent and Trademark Office*